United States Patent
Yang et al.

(10) Patent No.: US 8,480,945 B2
(45) Date of Patent: Jul. 9, 2013

(54) ELECTROSPINNING MANUFACTURE FOR DRUG CARRIERS

(75) Inventors: Chih-Hui Yang, Chiayi (TW); Keng-Shiang Huang, Chiayi County (TW); Yung-Sheng Lin, Changhua County (TW)

(73) Assignee: I-Shou University, Kaohsiung County (TW)

( * ) Notice: Subject to any disclaimer, the term of this patent is extended or adjusted under 35 U.S.C. 154(b) by 195 days.

(21) Appl. No.: 12/836,318

(22) Filed: Jul. 14, 2010

(65) Prior Publication Data

US 2012/0013046 A1 Jan. 19, 2012

(51) Int. Cl.
*B29C 47/00* (2006.01)
(52) U.S. Cl.
USPC ............................................................ 264/465
(58) Field of Classification Search
USPC .................................................. 264/497, 465
See application file for complete search history.

(56) References Cited

U.S. PATENT DOCUMENTS

2012/0009264 A1* 1/2012 Yang et al. ..................... 424/489

FOREIGN PATENT DOCUMENTS

| TW | 524699 | 3/2003 |
| TW | I283585 | 7/2007 |
| TW | 200740472 | 11/2007 |
| TW | I301415 | 10/2008 |
| TW | I301422 | 10/2008 |

OTHER PUBLICATIONS

Suksamran et al. ("Biodegradable alginate microparticles developed by electrohydrodynamic spraying techniques for oral delivery of protein" J. Microencapsulation, 2009; 26(7): 563-570.).*

* cited by examiner

*Primary Examiner* — Larry Thrower
(74) *Attorney, Agent, or Firm* — Muncy, Geissler, Olds & Lowe, PLLC

(57) ABSTRACT

An electrospinning manufacture for drug carriers is disclosed. The method comprises a preliminary step mixing a predetermined drug, an alginate, and a saline to obtain a mixture; an electric field establishing step providing a collection plate and an emitter filled with divalent cation agent and the mixture individually, wherein an electric field is applied to the collection plate and the emitter to form a voltage therebetween; and an electrospinning step sequentially dropping the mixture from the emitter into the divalent cation agent filled in the collection plate via the driving of the electric field, triggering a crosslinking-gelating reaction between the divalent cation and the alginate, wherein a plurality of gel particles is produced for a coating of the predetermined drug presenting a drug carrier performance.

5 Claims, 8 Drawing Sheets

ELECTROSPINNING MANUFACTURE FOR DRUG CARRIERS

BACKGROUND OF THE INVENTION

1. Field of the Invention

Figure 1:
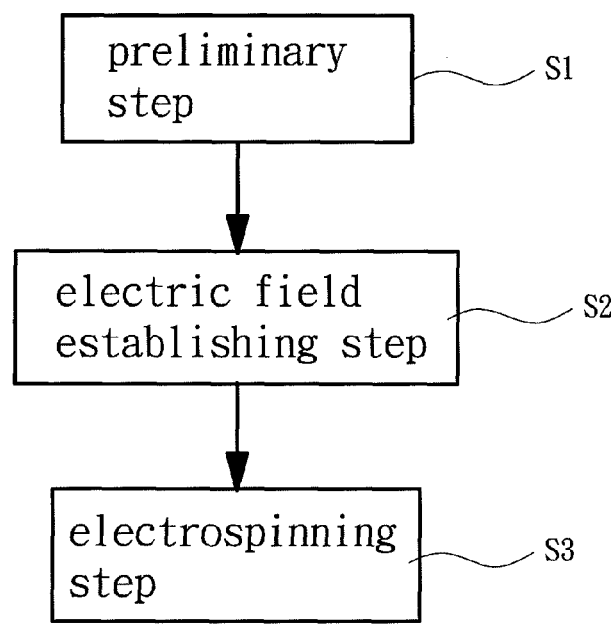

The present invention generally relates to an electrospinning manufacture for drug carriers and, more particularly, to an electrospinning manufacture for controlling the size and shape of produced drug carriers.

2. Description of the Related Art

In biotechnological manufacturing industry, due to the particular essential or function of the emerging protein drug, conventional drug transmission system may no longer be appropriate for drug delivery to individuals. (not be transmitted to a living body via conventional methods due to the special characteristics and effects thereof). Therefore, the development and application of the drug transmission system has become an important issue in recent decades. Mainly, the drug transmission system is designed to precisely control the function of a predetermined drug in right place and right time in order to reduce some predetermined side effects. (to an affected part so that the bioavailability of the predetermined drug is improved and the side effects of the predetermined drug are reduced.) Based on diverse requirements of technical platforms, the conventional drug carriers are mainly categorized into transplantation type, adhesion type and time-releasing type, as described below.

The transplantation-type drug carrier is mainly repairing or replacing the tissue damages of human body. The transplantation-type drug carrier is primarily from some natural or synthesized polymer such as collagen, chitosan, polyglycolide acid and so on. Generally, the polymers have biocompatibility and biodegradability which provide enough space for cell growth as implanted into human body. As disclosed in Taiwan Patent Number I283585a discloses a mixture containing bone cement powder, as well as tricalcium phosphate coated by chitosan particles, for facilitating regeneration of bone cells in order to improves the fixing effects and side effects of conventional bone powder.

The adhesion-type drug carrier is mainly for cell adhesion, with some synthesized materials including synthesized polyethylene, polyvinyl chloride and polymethacrylic acid resin manufactured as drug carriers especially for protein drugs. In this way, the cell growth and cell decomposition of the target part can be facilitated.

The time-releasing type drug carrier is primarily made form alginate. The alginate is a natural nonpoisonous polymer of polymeric saccharides belonging to unbranched polysaccharide. The alginate is capable to form colloids in a divalent cation agent to apply to various biological substances and medications, which subsequently performs at a coating behavior. For example, Taiwan Patent Number 524699 discloses a manufacturing method for producing a multi-ingredient particle of collagen and biochemical ceramic powder in which a mixture of a soluble collagen, a biomedicine ceramic powder and an alginate solution is dropped into a divalent cation agent to obtain some biological micromaterials via a cross-linking reaction between the mixture and the divalent cation agent.

On the other hand, the manufacturing method of conventional drug carriers is substantially categorized into dropping, emulsion and electrospinning. In the dropping method, a mixture of a predetermined drug and a polymer, such as alginate, is dropped into a cross-linked agent, such as a divalent cation agent in order to obtain particles of drug carrier via a crosslinking-gelating reaction between the mixture and the divalent cation agent. The particles of drug carrier obtained from the dropping method substantially have a diameter of 1.2 millimeter.

In the emulsion, a mixture of a polymer, a predetermined drug to be encapsulated, an emulsifier and a lipid is forced to pass through a hydrophobic membrane by a gaseous matter, so as to obtain emulsified drips. Sequentially, a cross-linked agent is added into the emulsified drips so that a crosslinking-gelating reaction of the polymer can be performed. In this situation, the particles may be dehydrated to obtain particle drug carriers with a diameter of about 200 millimeter. For instance, Taiwan Patent Number I301422 discloses a solidification process of the emulsion in which an emulsified solution and a solidification solution are prepared and injected into a Y-shaped crotched passageway to obtain drug carriers. In the solidification, the mixture of the emulsified solution and a solidification solution is preferably prepared in advance so as to shorten the reaction time period of solidification. In addition, smaller drug carriers are obtained by controlling the flow speed of the emulsified solution and a solidification solution in the Y-shaped crotched passageway.

However, since the above dropping and emulsion mechanisms produce the drug carriers in a random manner, the quantity and size of produced drug carriers are not easy to control. That is, the produced drug carriers tend to have different diameter and size. Therefore, the function and utility of the drug carriers can be interfered and unpredicted. Furthermore, the ratio of the ingredients and the manipulation steps must be accurately handled to ensure a desired process of the drug carriers. Therefore, longer manipulation time is required and the manufacturing process of the drug carriers tends to be affected by human factors. Therefore, the dropping and emulsion mechanisms are not suitable for industrial production in drug manufacturing industry.

The electrospinning technology is the emerging nanotechnology in recent years. It can rapidly and directly transform a polymer into a nanofiber usually in taper shape. The drug fibers are generally applied to surgical transplantations or for direct adhesion of wounded parts or for any other medical field. As an example, Taiwan Publication Number 200740472 discloses another nanofiber produced by electrospinning in which a mixture containing a fixed-ratio of a collagen, chitosan, polyethylene oxide and an acid solution is prepared and manufactured into nanofiber. The nanofiber may serve as a medical dressing for wounded parts which has better biocompatibility and larger surface area for facilitating the healing of the wounded parts.

However, the biomaterials produced by the electrospinning technology are only suitable for use in transplantation or in use as medical dressings due to the taper shape thereof. In other words, it is less efficient if applied to oral taking, inhaling or injection for treatments, thus limiting the use thereof.

Taiwan Patent Number I301415 discloses a nanometer-sized collagen produced by placing a collagen in a fluid environment with an electric field applied. The nanometer-sized collagen has a simpler manufacture process and is more easily to be absorbed by living bodies. Although the produced biomaterials are in particle form and easy to be absorbed by living bodies, they are used merely for cell regeneration. Therefore, the use thereof is still limited.

In recent years, more and more drug carriers are manufactured via electrospinning technology. During the manufacturing, a high-voltage electric field is applied to move a mixture of a predetermined drug and a chitosan liquor from a source to a cross-linking agent (which in generally is a salt liquor with metal ions), allowing the high polymer materials of the chitosan liquor to have a conjugation with the metal ions of the curing agent. In this way, the high polymer materials of the chitosan liquor may become a high polymer gel. Then, the predetermined drug is coated with the high polymer gel to form a particle drug carrier having a slow releasing function. Note the particle drug carrier is manufactured in a single step.

However, the particle drug carriers produced by the electrospinning have some drawbacks described below. Firstly, the particle drug carriers are manufactured via the interaction of the chitosan and the cross-linking agent. However, the chitosan stays positively charged only in an acid environment and may then be able to react with the electric field. Therefore, an acid liquor is required for melting the chitosan before the electrospinning technology is applied. However, the acid liquid has negative effects for specific components so that the effects of drug are impacted. Secondly, the intensity of the mechanical effect between the chitosan and the cross-linking agent is too weak to maintain the structure of the chitosan. Therefore, the produced drug carriers are in different shape. As a result, the effects of the drug carriers can't be accurately predicted when used in living bodies. Briefly speaking, although the electrospinning technology has simplest manufacturing process and best effects among the conventional drug carrier manufacturing technologies, some bottlenecks of manufacturing process still exist. Therefore, it is desired to improve the electrospinning technology.

SUMMARY OF THE INVENTION

It is therefore the primary objective of the invention to provide an electrospinning manufacture for drug carriers which produces drug carriers with consistent diameter.

It is another objective of the invention to provide an electrospinning manufacture for drug carriers which produces drug carriers with consistent size.

It is yet another objective of the invention to provide an electrospinning manufacture for drug carriers which produces drug carriers suitable for transmission of various biomaterials or medicaments.

It is yet another objective of the invention to provide an electrospinning manufacture for drug carriers which produces drug carriers with different shape and size in comply with the purposes of various predetermined drugs.

The invention discloses an electrospinning manufacture for drug carriers. The method comprises a preliminary step mixing a predetermined drug, an alginate, and a saline to obtain a mixture; an electric field establishing step providing a collection plate and an emitter filled with divalent cation agent and the mixture individually, wherein an electric field is applied to the collection plate and the emitter to form a voltage therebetween; and an electrospinning step sequentially dropping the mixture from the emitter into the divalent cation agent filled in the collection plate via the driving of the electric field, triggering a crosslinking-gelating reaction between the divalent cation and the alginate, wherein a plurality of gel particles is produced for a coating of the predetermined drug presenting a drug carrier performance.

BRIEF DESCRIPTION OF THE DRAWINGS

The present invention will become more fully understood from the detailed description given hereinafter and the accompanying drawings which are given by way of illustration only, and thus are not limitative of the present invention, and wherein:

FIG. 1 shows a flowchart of an electrospinning manufacture for drug carriers according to a preferred embodiment of the invention.

FIG. 2 shows a diagram of an electric field establishing step of the electrospinning manufacture according to the preferred embodiment of the invention.

FIG. 3 shows a relation between the magnitude of the electric field and the diameter of the drug carriers according to the preferred embodiment of the invention.

FIG. 4*a* shows a scanning electron microscope diagram of the drug carriers according to the preferred embodiment of the invention.

FIG. 4*b* shows another scanning electron microscope diagram of the drug carriers according to the preferred embodiment of the invention.

FIG. 5*a* shows an electron microscope diagram of the drug carriers according to the preferred embodiment of the invention.

FIG. 5*b* shows another electron microscope diagram of the drug carriers according to the preferred embodiment of the invention.

FIG. 5*c* yet shows another electron microscope diagram of the drug carriers according to the preferred embodiment of the invention.

FIG. 5*d* yet shows another electron microscope diagram of the drug carriers according to the preferred embodiment of the invention.

FIG. 5*e* shows an electron microscope diagram of the drug carriers after dehydration according to the preferred embodiment of the invention.

FIG. 5*f* shows another electron microscope diagram of the drug carriers after dehydration according to the preferred embodiment of the invention FIG. 5*g* yet shows another electron microscope diagram of the drug carriers after dehydration according to the preferred embodiment of the invention.

FIG. 5*h* yet shows another electron microscope diagram of the drug carriers after dehydration according to the preferred embodiment of the invention.

In the various figures of the drawings, the same numerals designate the same or similar parts. Furthermore, when the term "first", "second", "third", "fourth", "inner", "outer" "top", "bottom" and similar terms are used hereinafter, it should be understood that these terms are reference only to the structure shown in the drawings as it would appear to a person viewing the drawings and are utilized only to facilitate describing the invention.

DETAILED DESCRIPTION OF THE INVENTION

In the present invention an electrospinning manufacture is used to achieve the crosslinking-gelating reaction between the alginate and divalent cation so as to produce gel particles which a predetermined drug is coated with. In this way, a manufacturing process of drug carrier can be simplified, and more convenient in controlling the diameter, evenness and shape of the produced drug carriers. Referring to FIG. 1, a flowchart of the electrospinning manufacture comprising a preliminary step S1, an electric field establishing step S2 and an electrospinning step S3 is shown.

The preliminary step S1 is to mix a predetermined drug, an alginate and a saline to obtain a mixture for producing the drug carriers in later procedure. The alginate used in the embodiment is a natural polysaccharide and is mixed with the predetermined drug in a ratio of 2:1. The mixed predetermined drug and alginate has a total weight of 0.05 to 0.3 gram and is dissolved in a deionized water of 10 milliliter to obtain the mixture of 0.5 to 3 wt %. The alginate is negatively charged when dissolved in the deionized water. The negatively charged alginate may react with the divalent cation to form gel particles for coating of cells and drugs. The gel particles may enable slow movement of the cells and drugs, achieving the slow releasing of the cells and drugs.

Figure 2:
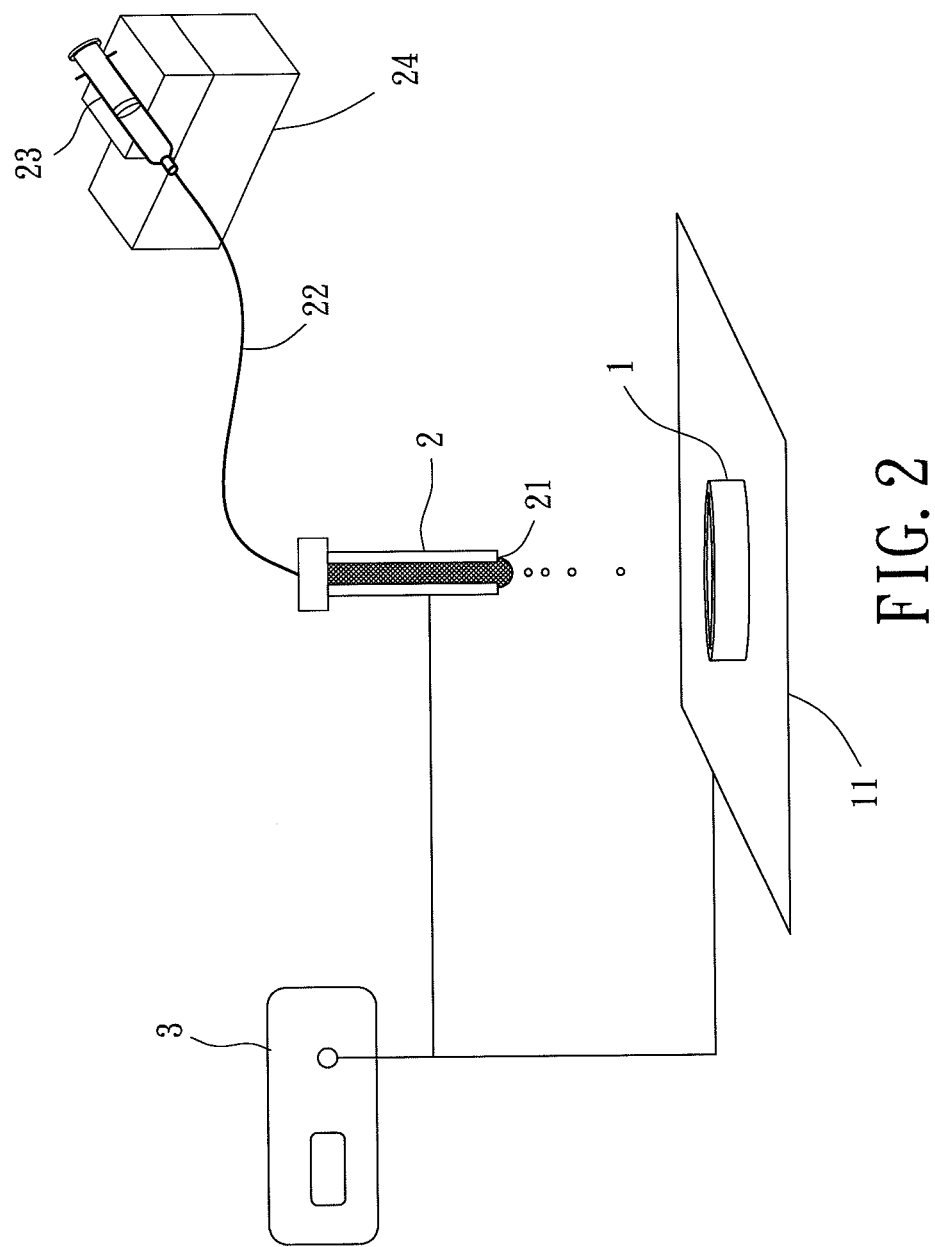

Referring to FIG. 2, the electric field establishing step S2 provides a collection plate 1 and an emitter 2. The collection plate 1 is filled with the divalent cation agent and the emitter 2 is filled with the mixture. A voltage is applied between the collection plate 1 and emitter 2 to form an electric field. The collection plate 1 and emitter 2 are preferably disposed along a veridical direction, with the emitter 2 being above the collection plate 1 by a proper distance. In this way, the mixture in the emitter 2 may drop into the collection plate 1 via an opening 21 of the emitter 2. The collection plate 1 comprises a metal plate 11 with electricity conductivity. The metal plate 11 may be connected to a polarity of a power supplier 3 via a wire, and the emitter 2 may be connected to another polarity of the power supplier 3 via the wire.

In the embodiment, the mixture is firstly injected into an injection member 23. Then, a pump 24 provides a force to push the injection member 23, enabling the mixture of the injection member 23 to flow to the emitter 2 via a soft pipe 22. The magnitude of the force of the pump 24 may be controlled so that the speed of the mixture flowing out of the emitter 2 may be adjusted. Preferably, the mixture may flow out of the emitter 2 with a speed of 0.5 to 3 milliliter per hour. At this moment, the distance between the opening 21 of the emitter 2 and the collection plate 1 is 10 centimeter. Following, the power supplier 3 is turned on, with a positive electrode thereof having a voltage of 1 to 15 KV (kilo-volt) and a negative electrode thereof having a voltage of 0V. In this way, an electric field is formed between the collection plate 1 and emitter 2. The electric field is 10 to 150 KV per meter.

The electrospinning step S3 uses the electric field to push the mixture out of the opening 21 of the emitter 2, as shown in FIG. 2. In this moment, the pushed mixture may cohere as a few drips due to a surface tension thereof. Also, the high voltage applied to the emitter 2 may pull all the charges of the alginate from the interior of the mixture to the surface of the mixture. As a result, the surface of the mixture accumulates a lot of pulled charges. By the time a voltage generated by the accumulated charges exceeds a threshold value, the voltage may overcome the surface tension of the mixture and thus restrains the volume of the drips. In this way, the volume of the drips may remain in a nanometer scale. The drips will be attracted by the low potential of the collection plate 1 and thus fall from the opening 21 of the emitter 2. Finally, the falling drips will be collected by the collection plate 1 and mixed with the divalent cation agent of the collection plate 1. At this moment, the alginate contained in the falling drips may have a crosslinking-gelating reaction with the divalent cation agent to form the gel particles. The predetermined drug is eventually coated with the gel particles to form drug carriers.

Figure 3:
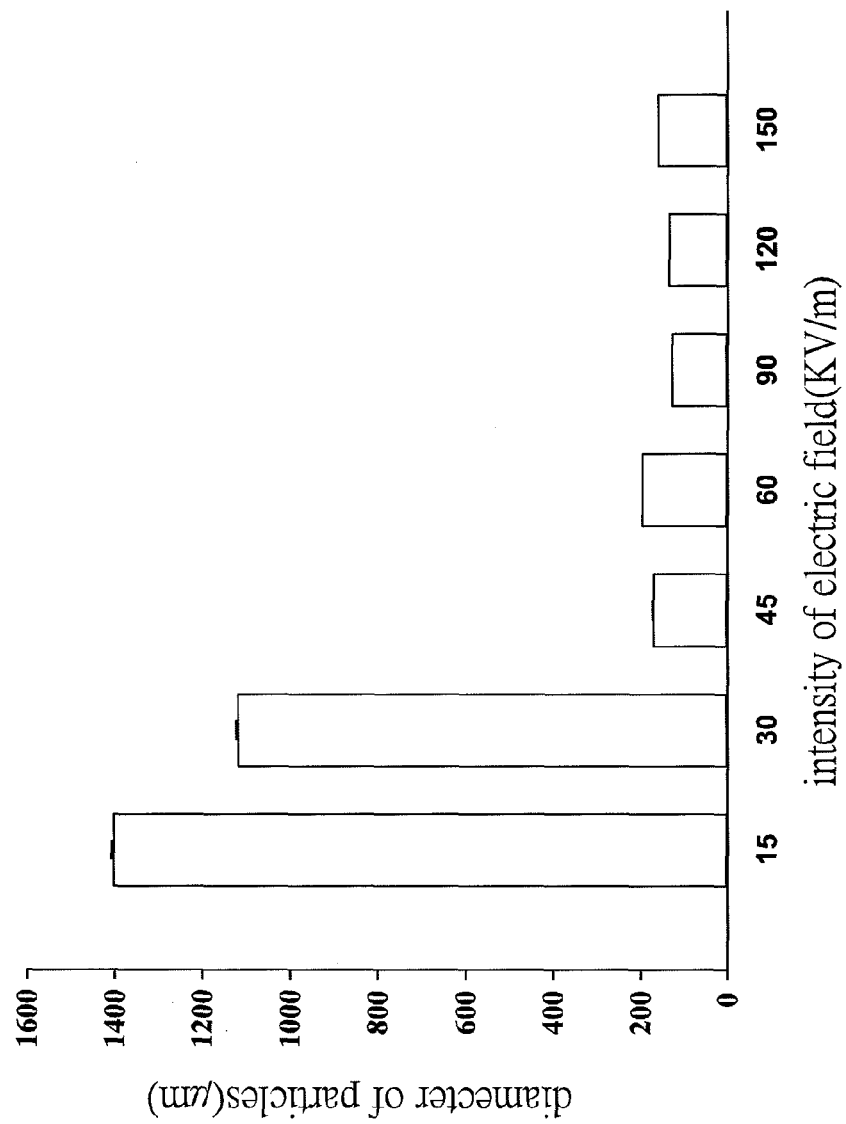

In the embodiment, the magnitude of the electric field may be adjusted to control the diameter and evenness of the produced drug carriers. Referring to FIG. 3, a diagram illustrating a relation between the magnitude of the electric field and the diameter of the drug carriers is shown. Based on the FIG. 3, when the magnitude of the electric field is 15 to 30 KV/m and the flow speed is 1 milliliter per hour, the drug carriers formed in the divalent cation agent (calcium chloride agent) have larger diameter in average, which is about 1100 to 1500 μm (micrometer). In another case where the magnitude of the electric field is 45 to 150 KV/m under otherwise identical conditions, the drug carriers have relatively smaller diameter in average, with the smallest one being about 120 to 200 μm.

Figure 4A:
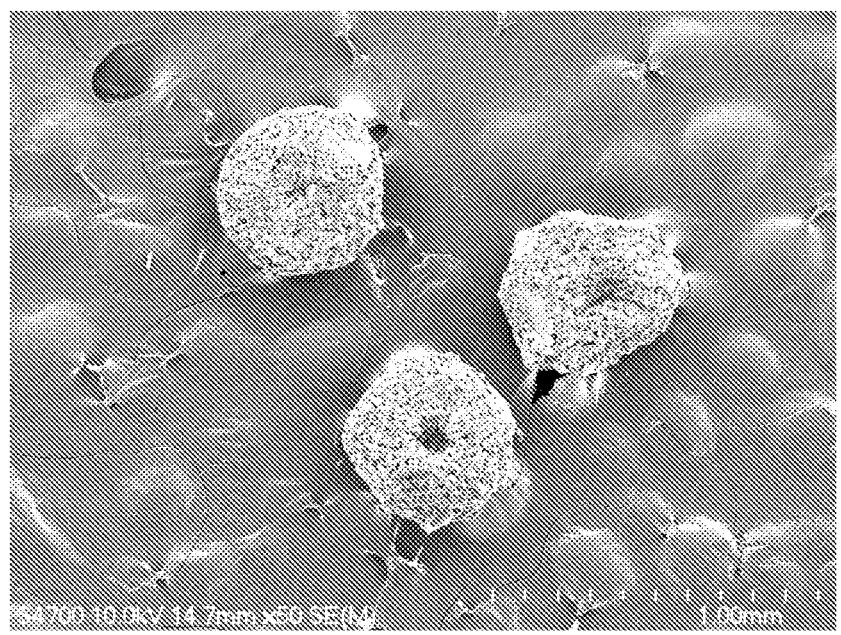
Figure 4B:
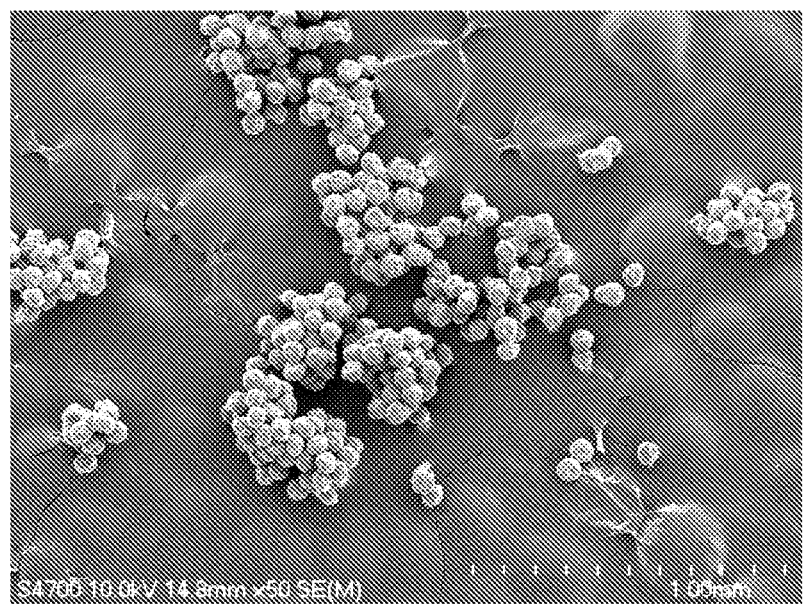

Referring to FIGS. 4a and 4b, two scanning electron microscope (SEM) diagrams illustrating the drug carriers respectively produced with a strong electric field and a weak electric field are shown. The drug carriers produced with the strong electric field (150 KV/m) shown in FIG. 4a obviously have larger diameter compared to those produced with the weak electric field (15 KV/m) shown in FIG. 4b. This diameter difference is substantially in 7 times. Therefore, it is proven that the diameter of the drug carriers may vary based on the magnitude of the electric field. The magnitude of the electric field may be changed based on the types of the predetermined drug.

Figure 5A:
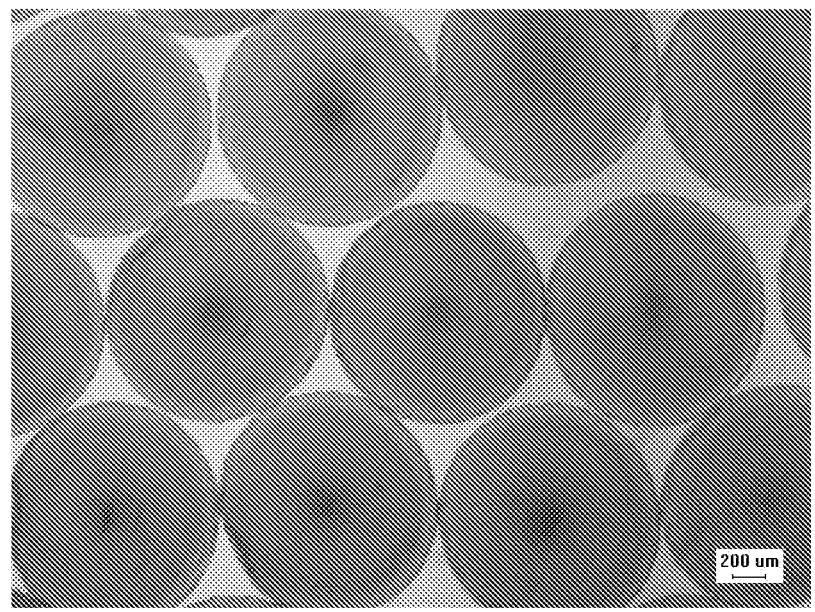
Figure 5B:
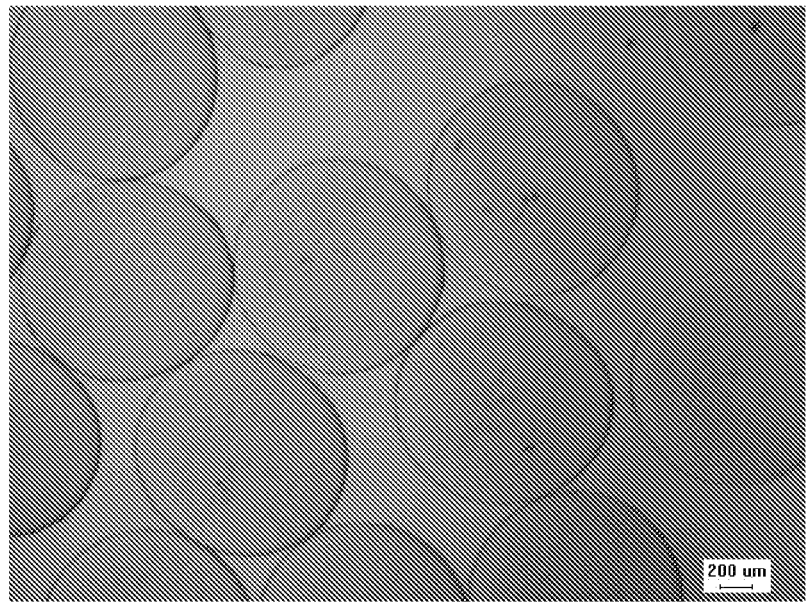
Figure 5C:
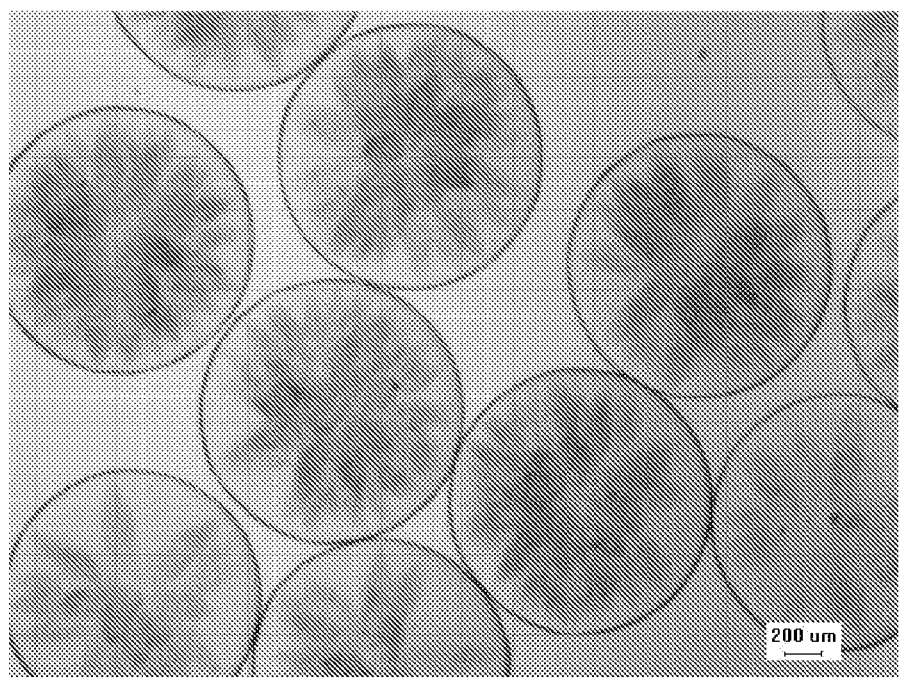
Figure 5D:
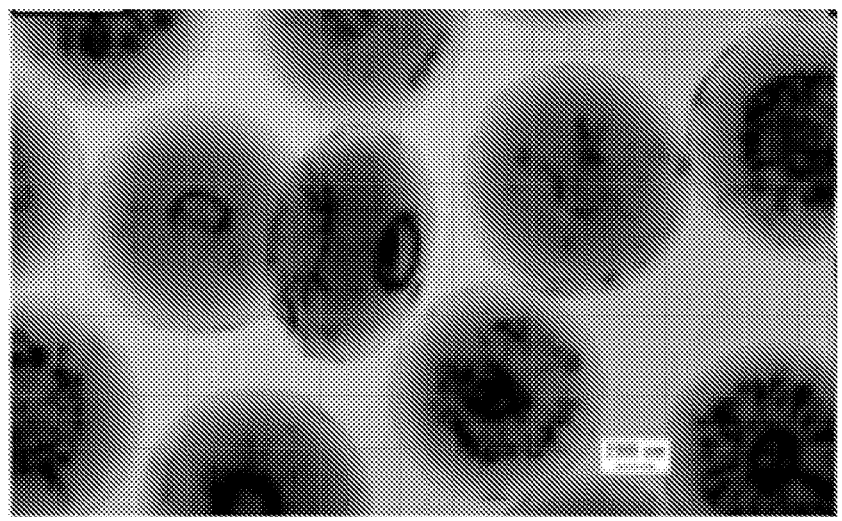

Moreover, different divalent cation may result in somewhat different crosslinking-gelating reaction with the alginate, relatively affecting the generated gel particles and the coating of the predetermined drug. Therefore, different divalent cation may result in different shape of the drug carriers. Based on this, the divalent cation agent may be selected based on the use of the predetermined drug. Referring to FIGS. 5a to 5h, four different divalent cation agents, which are 5 to 25% of copper sulfate agent (FIG. 5a), calcium chloride agent (FIG. 5b), barium chloride agent (FIG. 5c) and ferric chloride agent (FIG. 5d), respectively undergo the crosslinking-gelating reaction with the alginate to produce various drug carriers with different shape. The drug carriers produced in the four divalent cation agents all have the same evenness and fineness but different shape. For example, as shown in FIG. 5d, the drug carriers produced in the ferric chloride agent have substantially oval shape.

Figure 5E:
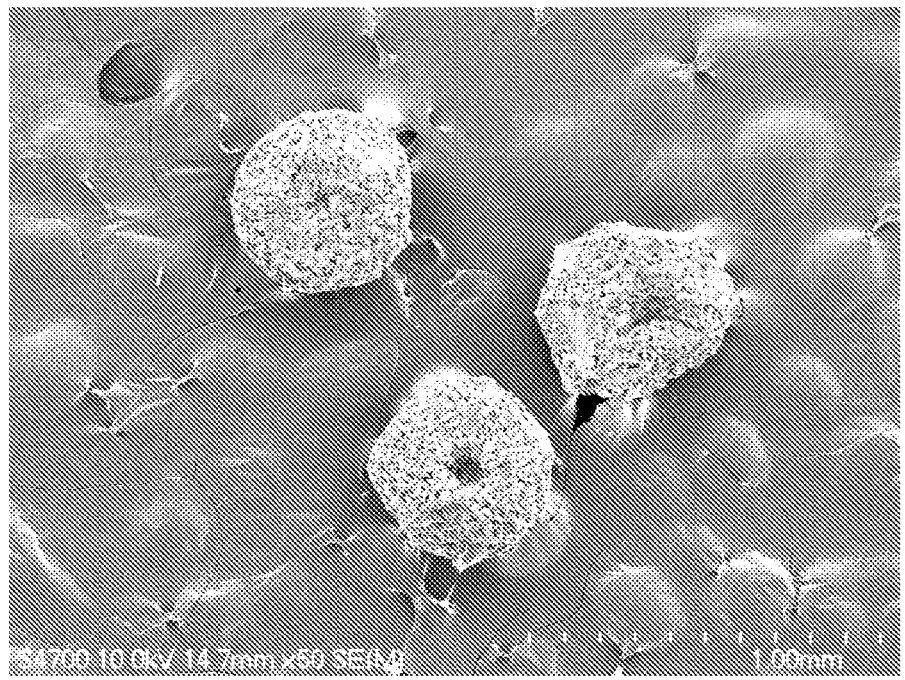
Figure 5F:
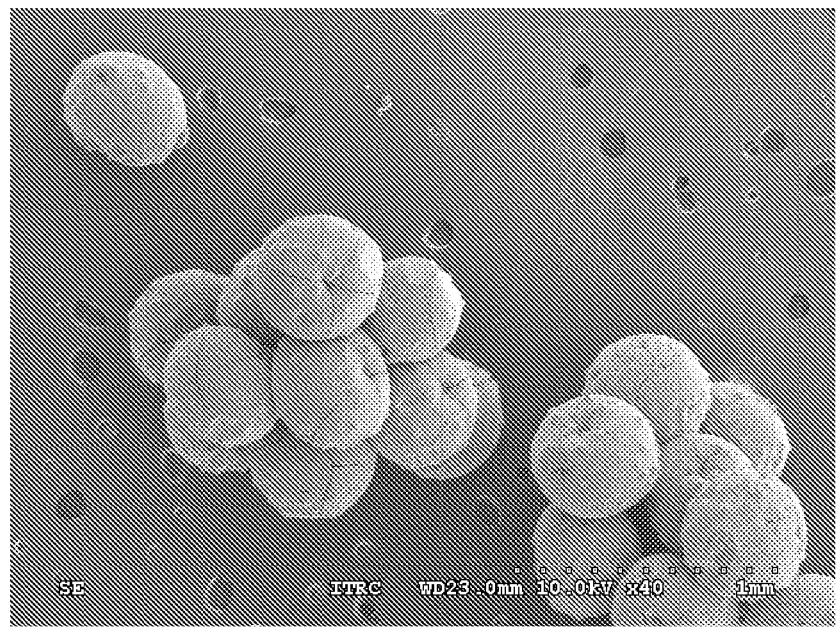
Figure 5G:
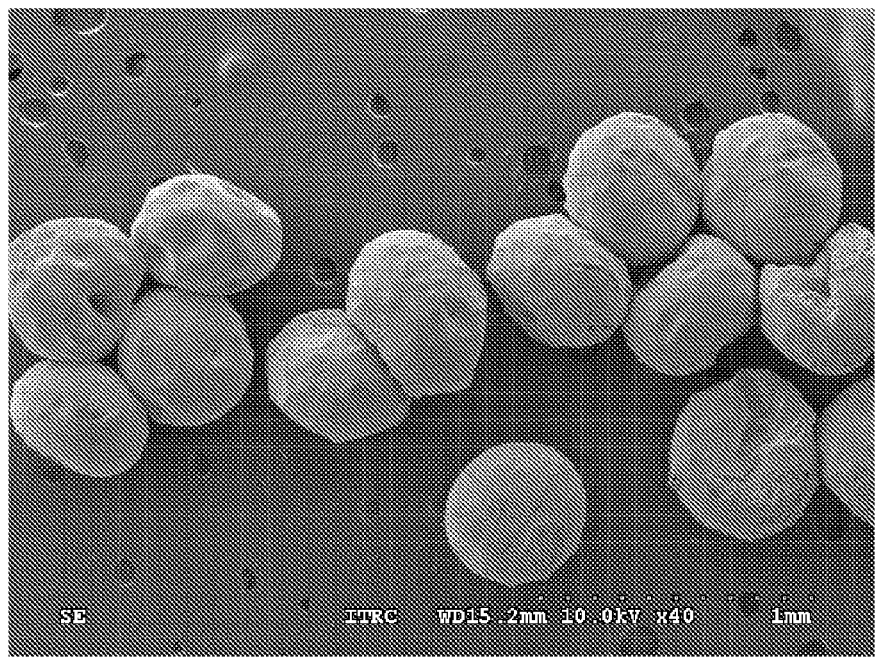
Figure 5H:
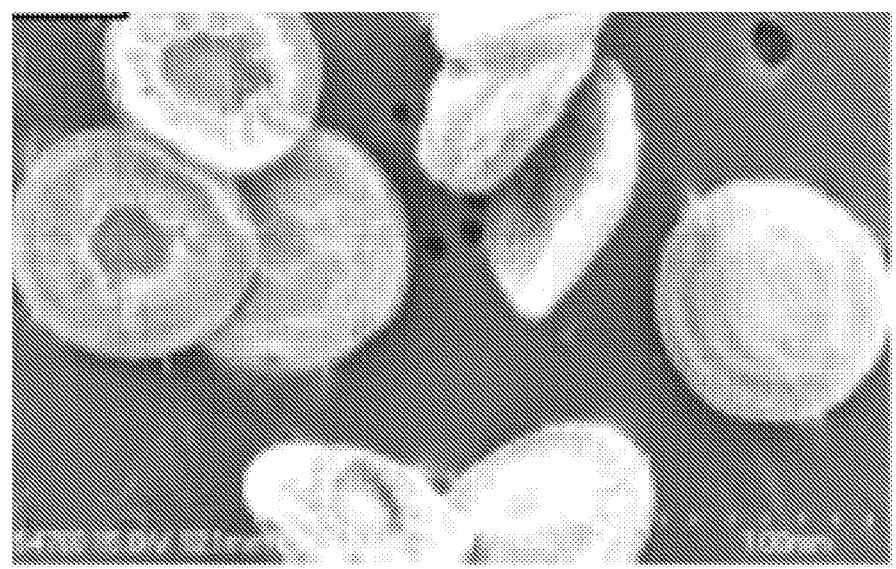

Referring to FIGS. 5e to 5h also, the shape difference of the drug carriers produced in the four divalent cation agents, after dehydration, may be observed via the SEM. Specifically, as shown in FIG. 5e, the drug carriers produced in the copper sulfate liquor appear to be in a round shape after dehydration. As shown in FIG. 5f, the drug carriers produced in the calcium chloride agent appear to be in a grape-like shape after dehydration. As shown in FIG. 5g, the drug carriers produced in the barium chloride agent appear to be in a ball-like shape after dehydration. As shown in FIG. 5h, the drug carriers produced in the ferric chloride agent appear to be in a circular-plate shape after dehydration.

The alginate of the invention may remain negatively charged when dissolved in the saline, which provides a change to react with an electric field without using general acid or alkaline liquor. The saline won't affect the character of the predetermined drug and thus won't interfere with the effects of the predetermined drug. Therefore, the alginate of the invention may be used for various drugs without interfering with the effects of the drugs. In the invention, the alginate has a stronger crosslinking-gelating reaction with the divalent cation, which enables the gel particles to have sufficient mechanical strength for maintaining the structure of the produced drug carriers. Therefore, the shape and shape of the drug carriers are more regular. In addition, the diameter and evenness of the drug carriers may be efficiently controlled via the electric field, which allows the production of the drug carriers with consistent size, diameter and shape. Hence, the releasing speed and condition of the predetermined drug in a living body may be accurately predicted and the effects of the predetermined drug in the living body may be evaluated.

As described above, different divalent cation agents may be selected to obtain different-shape drug carriers having different movement, releasing speed and functioning in a living body, which results in different effects and functioning of the predetermined drug in the living body. Different-shape drug carriers may achieve different releasing speed in comply with the functions and purposes of the predetermined drugs. Thus, the use of the proposed drug carriers is more flexible.

The proposed electrospinning mechanism manufactures drug carriers with even diameter via the crosslinking-gelating reaction between the alginate and divalent cation, enabling the accurate prediction of the releasing of the drug carriers in a living body. In addition, the diameter of the drug carriers may be adjusted according the needs, thus accomplishing the slow releasing of the drug carriers.

The proposed electrospinning mechanism manufactures drug carriers with regular shape, achieving the stability of slow releasing of the drug carriers in a living body.

The proposed electrospinning mechanism uses a saline to dissolve the alginate particles, wherein the dissolved alginate in the saline won't affect the character of a predetermined drug and is therefore suitable for the coating of various biomaterials and medicaments. Thus, the use of safety is secured.

The proposed electrospinning mechanism uses different divalent cation agents to produce different-shape drug carriers having different slow releasing effects in comply with the purposes of various predetermined drugs. Thus, the drug carriers may have a variety of applications.

Although the invention has been described in detail with reference to its presently preferable embodiment, it will be understood by one of ordinary skill in the art that various modifications can be made without departing from the spirit and the scope of the invention, as set forth in the appended claims.

What is claimed is:

1. An electrospinning manufacture for drug carriers, comprising:
   a preliminary step mixing an alginate with a predetermined drug in a ratio of 2:1 and then dissolving the mixed predetermined drug and alginate in a saline to obtain a mixture wherein a combined weight of the predetermined drug and the alginate is 0.5 to 3 wt % in the saline;
   an electric field establishing step providing a collection plate and an emitter, filled with divalent cation agent and the mixture, respectively, wherein a voltage is applied to the collection plate and the emitter to form an electric field from 45 to 150 KV/m therebetween; and
   an electrospinning step sequentially dropping the mixture from the emitter into the divalent cation agent filled in the collection plate with a speed of 0.5 to 3 milliliter per hour via the driving of the electric field, triggering a crosslinking-gelating reaction between the divalent cation and the alginate to form a gel coating serving as a drug carrier.

2. The electrospinning manufacture for drug carriers as defined in claim 1, wherein during the preliminary step, a selecting step is performed to select the divalent cation agent as calcium chloride.

3. The electrospinning manufacture for drug carriers as defined in claim 1, wherein during the preliminary step, a selecting step is performed to select the divalent cation agent as copper sulfate.

4. The electrospinning manufacture for drug carriers as defined in claim 1, wherein during the preliminary step, a selecting step is performed to select the divalent cation agent as barium chloride.

5. The electrospinning manufacture for drug carriers as defined in claim 1, wherein during the preliminary step, a selecting step is performed to select the divalent cation agent as ferric chloride.

* * * * *